United States Patent [19]

Edwards

[11] Patent Number: 5,772,346
[45] Date of Patent: Jun. 30, 1998

[54] LIQUID APPLICATOR WITH STRUCTURAL INSERT

[75] Inventor: William R. Edwards, El Paso, Tex.

[73] Assignee: Medi-Flex Hospital Products, Inc., Overland Park, Kans.

[21] Appl. No.: 837,653

[22] Filed: Apr. 22, 1997

[51] Int. Cl.⁶ ............................ A61M 35/00; A47L 13/34
[52] U.S. Cl. .............................. 401/132; 604/3; 401/133; 401/135
[58] Field of Search .................................... 401/132, 135; 604/3

[56] References Cited

U.S. PATENT DOCUMENTS

| | | |
|---|---|---|
| 3,466,131 | 9/1969 | Arcudi . |
| 3,768,916 | 10/1973 | Avery . |
| 3,774,609 | 11/1973 | Schwartzman ............................... 604/3 |
| 3,998,559 | 12/1976 | Hoyt ........................................ 401/132 |
| 4,183,684 | 1/1980 | Avery, Jr. . |
| 4,475,835 | 10/1984 | Verboom et al. ....................... 401/132 |
| 4,784,506 | 11/1988 | Koreska et al. . |
| 4,878,775 | 11/1989 | Norbury et al. ........................ 401/132 |
| 4,899,739 | 2/1990 | Konishi . |
| 5,147,337 | 9/1992 | Plone . |
| 5,538,353 | 7/1996 | DeHavilland . |

*Primary Examiner*—Charles R. Eloshway
*Attorney, Agent, or Firm*—Shook, Hardy & Bacon L.L.P.

[57] ABSTRACT

A liquid applicator for applying a desired liquid to a surface includes a closed ampule formed of a fracturable material containing the desired liquid, a body having a pocket with an open side and a shape adapted to receive the ampule, and a porous element sealed to the body and closing off the open side of the pocket so that liquid flows through the element when the ampule is fractured. The body includes a pair of side walls that are spaced from one another in a first direction to define the pocket, and a pair of gripping members, are provided, which can be pivoted to fracture the ampule during use. The porous element is laminated with a material that does not stretch in the first direction, and the laminate material is secured between the side walls of the body to define a structural insert that prevents the side walls from pulling apart from one another when the gripping members are pivoted.

7 Claims, 1 Drawing Sheet

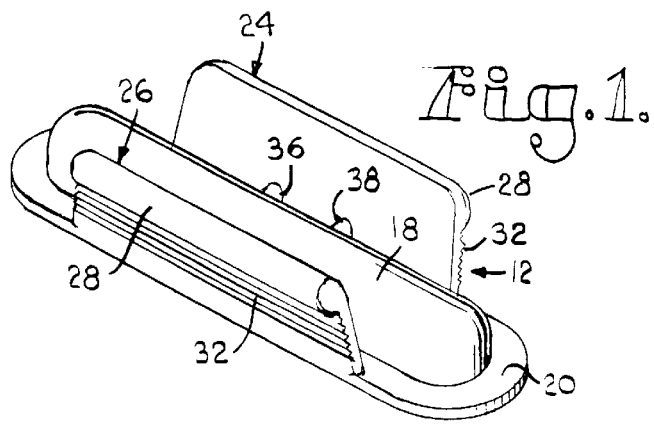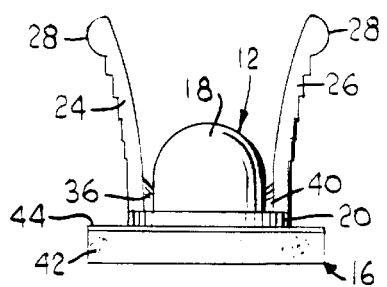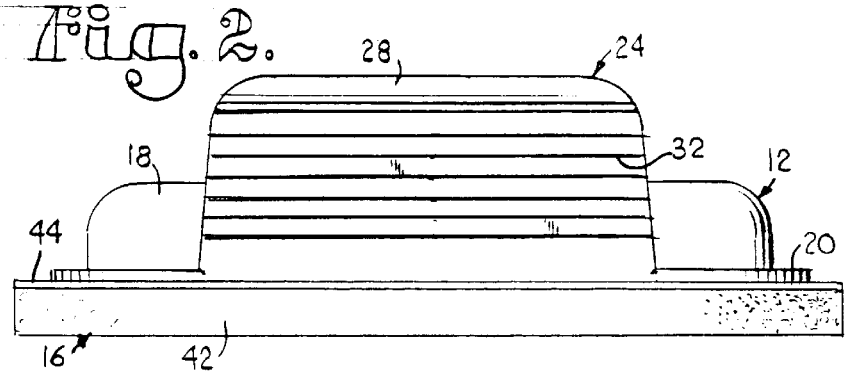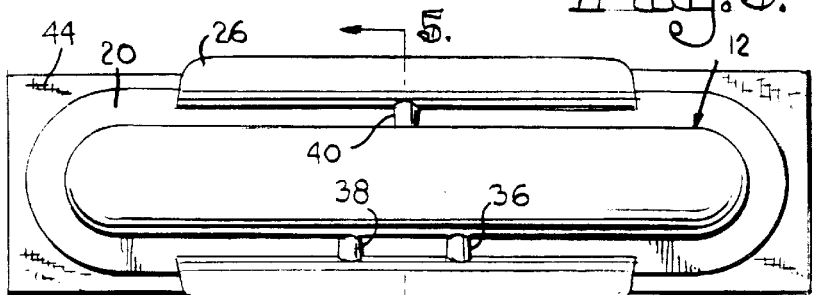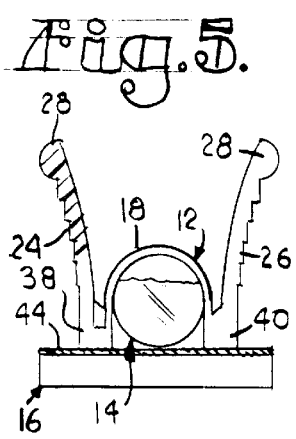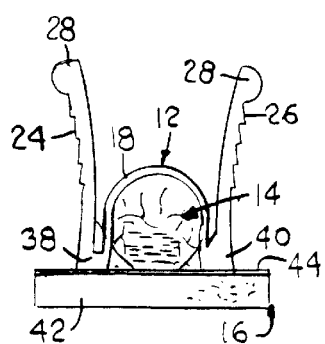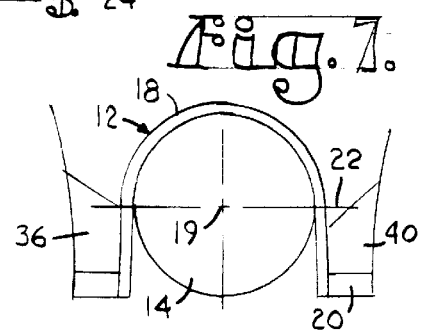

5,772,346

LIQUID APPLICATOR WITH STRUCTURAL INSERT

BACKGROUND OF THE INVENTION

The present invention relates generally to liquid applicators and, more particularly, to a hand-held liquid applicator having a pocket within which a liquid-filled, glass ampule is received, and a mechanism for fracturing the ampule to release the liquid for dispensing.

It is known to provide liquid applicators for applying liquids, such as medicaments or cleansing agents, wherein the applicator includes a body defining an open-sided pocket, a frangible ampule retained within the pocket, and a porous element overlying the pocket and enclosing the ampule. The liquid-filled ampule is formed of glass and can take a variety of shapes. The body includes a shaped wall that conforms generally with the shape of the ampule to define the open-sided pocket, and a flange extends from the shaped wall around the periphery of the pocket. In such applicators, the liquid-filled ampule is fractured by the user grasping the shaped wall and exerting a squeezing force that deforms the wall directly against the ampule. Of course, the squeezing force necessary to fracture the ampule depends on a number of factors such as the shape of the ampule, the materials used, and the location at which the force is exerted. Examples of this general type of applicator is illustrated in U.S. Pat. Nos. 3,466,131, to Arcudi; and 4,183,684, to Avery, Jr.

One problem experienced in these conventional constructions is that shards or pieces of the fractured ampule have a tendency to penetrate the shaped wall and injure the user's fingers. This can occur when the user over-exerts the squeezing pressure applied on the shaped wall. Further, the shaped wall is often difficult to grasp and hold onto when exerting the squeezing pressure or when applying the liquid to a surface, especially when the ampule is spherical in shape or of a small cylindrical configuration. Additionally, in such applicators, when the shaped wall is squeezed to fracture the ampule, nothing prevents the ampule from being pushed toward the open side of the cavity. Thus, the ampule is able to move around within the pocket when the wall is squeezed, sometimes avoiding fracture. Such movement towards the open side of the cavity may also occur after the ampule has been fractured, causing shards of the fractured ampule to poke into or through the porous element. In situations where the applicator is used to apply a liquid to the skin of a patient, shards of glass protruding into or through the sponge present a risk of injury.

Responsive to these problems, liquid applicators have been developed which include shaped walls having inward projections that engage the periphery of the ampule to maintain the ampule within the cavity and to prevent untoward movement of shards of glass through the sponge when fracturing of the ampule is effected. Further, applicators have been developed with shaped walls presenting a region to be grasped and squeezed by the user which provide a fulcruming effect so that the user squeezes the shaped wall at a location that is not directly in contact with the ampule. In other words, the ampule is fractured at a location that is spaced from the portion of the wall that is squeezed by the user. However, the possibility still exists that a user will over-squeeze the shaped wall causing pieces of the fractured ampule to shift to the region of squeezing and penetrate the wall. Although such liquid applicators represent an improvement over earlier conventional devices, there is a need to provide a liquid applicator that fully eliminates the risk of the user being injured by shards of glass penetrating the shaped wall or porous element. Further, there is a need for a liquid applicator that has improved structure for gripping the applicator so that it is easy and safe to use.

OBJECTS AND SUMMARY OF THE INVENTION

Thus, it is an object of the present invention to provide an improved hand-held applicator which permits the user to apply a squeezing force on the body at a location remote from the shaped wall defining the pocket. It is another object of the present invention to provide a member or members for gripping the applicator which enhance handling of the applicator while permitting the aforementioned remote squeezing, and that maintains the ampule within the body and prevents untoward movement of the ampule through the sponge when the gripping members are squeezed.

Another object of the invention is to provide a structural insert between opposed side walls of the body for preventing the side walls from pulling apart from one another when the squeezing force is applied to the gripping members, thus ensuring that the squeezing force is transmitted directly to the body to fracture the ampule.

In accordance with these and other objects evident from the following description of a preferred embodiment of the invention, the liquid applicator includes a body having a pair of side walls that are spaced from one another in a first direction to define a pocket, a closed ampule received in the pocket, and a lever presenting a first end secured to one of the side walls, a second free end, and an intermediate tappet that bears against the body and fractures the ampule when the lever is pivoted. A porous element covers the pocket so that liquid stored in the ampule flows through the porous element when the ampule is fractured. The porous element is laminated with a material that does not stretch in the first direction, and the laminate material is secured directly to and extends between the side walls of the body to prevent the side walls from pulling apart from one another when the lever is pivoted.

By providing a liquid applicator in accordance with the present invention, numerous advantages are realized. For example, by employing a porous element that is laminated with a material that does not stretch in the direction of spacing of the side walls, the laminate material defines a structural insert that prevents the side walls from pulling apart from one another when a fracturing force is applied to the lever. As such, the magnitude of the force required to fracture the ampule is reduced relative to applicators having no such insert. In addition, the reinforcement provided by the insert results in more consistent fracturing of ampules from applicator to applicator.

Further, by providing a porous element having a laminate, material is presented at the interface between the porous element and the body that can be melted to the material of the body to secure the porous element in place. As such, no adhesives or other fastening expedients are required to hold the pieces together. The laminate material also presents a physical barrier adjacent the ampule that prevents shards or fractured pieces of glass from penetrating into or through the porous element.

In a preferred construction, a pair of gripping members are provided which provide a mechanical advantage as they are pivoted toward one another, and the members concentrate the fracturing force on the ampule. This mechanical advantage results from the provision of retaining and breaking tappets which localize the pressure exerted on the relatively large gripping members, increasing the pressure exerted on the ampule at the tappets. As a result of this localization of the fracturing pressure exerted by the user, the ampule actually shatters with a distinct audible "pop", and the liquid contained in the ampule saturates the porous element, eliminating the conventional practice of repeatedly squeezing the applicator to force liquid from the ampule.

BRIEF DESCRIPTION OF THE DRAWING FIGURES

A preferred embodiment of the invention is described in detail below with reference to the attached drawing figures, wherein:

FIG. 1 is a perspective view of a body element forming a part of a liquid applicator constructed in accordance with the preferred embodiment;

FIG. 2 is a side elevational view of the liquid applicator;

FIG. 3 is a top plan view of the applicator;

FIG. 4 is a front elevational view of the applicator;

FIG. 5 is a cross-sectional view taken along line 5—5 of FIG. 3, illustrating a pair of levers forming a part of the applicator;

FIG. 6 is a cross-sectional view similar to FIG. 5, illustrating the levers pivoted to an ampule-fracturing position; and FIG. 7 is a schematic cross-sectional view of the applicator, illustrating the orientation of a pair of tappets forming a part of the applicator.

DETAILED DESCRIPTION OF THE PREFERRED EMBODIMENT

Turning initially to FIG. 5, a liquid applicator constructed in accordance with the preferred embodiment is illustrated as broadly including a body 12, a closed, liquid-filled ampule 14 received in the body 12, and a porous element 16 secured to the body 12 and enclosing the ampule 14 within the body 12 so that liquid flows through the element 16 when the ampule 14 is fractured.

The ampule 14 can be used for containing various liquids such as medicaments, cleansing agents, cosmetics, polishes, window treatments or the like. In one application of the preferred embodiment, the ampule 14 contains an antiseptic solution to be applied to a patient's skin prior to surgery. The antiseptic solution includes silicon that is utilized to dry the patient's skin and serve as a partial adhesive for a tape-like sheet that is placed on the patient to facilitate suturing of the patient once surgery is completed. Although the ampule 14 is illustrated as an elongated cylinder, it will be appreciated that the principles of the present invention may also be applied to spherical or elongated polygonal ampules. Preferably, the ampule 14 is formed of glass, although other fracturable materials are within the scope of the present invention. The wall of the glass ampule 14 is of a thickness sufficient to contain the desired liquid during transport and storage, yet allow the ampule to be fractured upon the application of sufficient localized pressure.

With reference to FIG. 2, the body 12 is preferably formed of high density polyethylene, although any material exhibiting similar flexibility and integrity may be used. The body 12 includes an open-sided pocket 18 within which the ampule is received and a flange 20 protruding from the pocket 18 along the open side thereof. The pocket 18 has a shape generally conforming to the shape of the ampule 14, as shown in FIG. 5. Accordingly, as shown in FIG. 7, the preferred pocket 18 is elongated and has a pair of laterally spaced side walls that are connected together by a U-shaped top wall. The pocket defines a longitudinal axis 19 that is generally collinear with the central longitudinal axis of the ampule 14 and an axial plane 22 which includes the pocket axis and is generally parallel to the flange 20.

As shown in FIG. 1, the body also includes a pair of elongated gripping members 24, 26 projecting from the flange 20 and having a wing-like configuration. The members 24, 26 run along the length of the pocket and are each spaced from the pocket 18 on opposite sides thereof. Along the upper free edge of each of the members 24, 26, ribs 28 jut laterally outward to facilitate handling of the applicator. Further, each of the members 24, 26 are provided with a relatively large, textured outer surface to prevent slippage from the user's hand during application, which in the illustrated embodiment takes the form of a series of steps 32. As shown in FIG. 4, the flange 20 supports the gripping members 24, 26 for pivoting movement relative to the pocket 18. Accordingly, the gripping members 24, 26 define levers that may be grasped by the user and pivoted toward one another against the pocket, and this pivoting movement is accommodated by the flexibility of the material forming the body.

As shown in FIG. 3, the body also includes structure for fracturing the ampule. Preferably, the structure includes a pair of breaking tappets 36, 38 and a retaining tappet 40 interposed between the gripping members 24, 26 and the pocket 18. The breaking tappets 36, 38 interconnect the flange 20, the gripping member 24 and the pocket. Moreover, as shown in FIGS. 4–7, the breaking tappets 36, 38 each include an upper edge that angles inwardly and downwardly from the gripping member 24 to a location along the side wall of the pocket 18 generally corresponding to the axial plane 22. Similarly, the retaining tappet 40 interconnects the flange 20, the gripping member 26 and the pocket 18. However, the upper edge of the retaining tappet 40 angles inwardly and downwardly from the gripping member 26 to a location along the pocket 18 below the axial plane 22 and above the flange 20, as shown in FIG. 7.

As shown in FIG. 2, all of the tappets 36, 38, 40 have a very short length relative to the length of the gripping members 24, 26 so that when the gripping members 24, 26 are pivoted toward one another by the user, the tappets 36, 38, 40 deform the pocket inwardly at positions immediately adjacent the tappets to exert inward forces against the ampule. In other words, the textured outer surfaces of the gripping members 24, 26 present a gripping area which is significantly larger than the area of the tappets which deform the pocket 18 inwardly, thereby localizing the forces effected by squeezing the members 24, 26, and enhancing fracturing of the ampule.

More particularly, the configuration of the breaking tappets 36, 38 causes the portion of the pocket extending from the axial plane 22 to the flange 20 to move inwardly at the tappets 36, 38. The inwardly moving pocket 18 engages the outermost point of the ampule 14 to exert localized fracturing forces against the ampule 14 that are generally vertically aligned with its central axis. The fracturing forces applied by the breaking tappets 36, 38 do not cause the ampule 14 to move toward or away from the open side of the pocket 18. On the other hand, the retaining tappet 40 causes a portion of the pocket 18 extending from the flange 20 to a location between the flange 20 and axial plane 22 to move inwardly in the region of the tappet 40. The inwardly moving pocket 18 effected by the retaining tappet 40 engages the ampule 14 at a point offset beneath the axial plane 22, thereby exerting a localized fracturing force against the ampule 14 which pushes the ampule 14 away from the open side of the pocket 18. Thus, the configuration of the retaining tappet 40 maintains the ampule 14 within the pocket when the gripping members 24, 26 are pivoted toward one another to fracture the ampule 14 so that the ampule does not shift prior to experiencing the localized fracturing forces being applied thereon.

As best shown in FIG. 3, the retaining tappet 40 is centrally disposed along the length of the pocket 18. Preferably, the breaking tappets 36, 38 are spaced axially from the retaining tappet 40 and from one another on opposite sides of the tappet 40. The relative positioning of the tappets 36, 38, 40 concentrates the fracturing forces in a somewhat triangular pattern, enhancing the fracturing of the ampule 14. However, it will be appreciated that the principles of the present invention are equally applicable to various other structure for fracturing the ampule 14.

The porous element 16 is secured to the body 12 over the open side of the pocket 18 and encloses the ampule 14 within the pocket so the liquid flows from the pocket 18 and through the element 16 when the ampule 14 is fractured. With reference to FIG. 5, the porous element is formed of felt or an open-celled foam material 42 that is laminated on the side facing the body with a material 44 that resists stretching in the direction transverse to the axis of the pocket. As such, the laminate material 44 acts as a structural insert extending between and connecting the side walls of the body together to prevent the side walls from pulling apart from one another when the gripping members are squeezed.

Preferably, the laminate material 44 is a polyester fabric that is resistant to stretching in one direction, referred to as the machine direction of the fabric, and that is stretchable in the direction transverse to the machine direction. By orienting the fabric on the porous element with the machine direction of the fabric extending in a direction perpendicular to the longitudinal axis of the pocket, the fabric resists stretching in the direction transverse to the axis of the pocket, preventing the side walls of the body from pulling apart under the squeezing force exerted on the gripping members.

The porous element 16 is secured to the body of the applicator by welding the fabric laminate material 44 to the flange 20 of the body using an ultrasonic welding operation. The polyester material of the laminate provides suitable welding material that melts together with the material of the flange to secure the porous element in place over the pocket and enclose the ampule 14. Other suitable securing expedients could be employed in place of the ultrasonic welding operation. For example, the porous element could be secured in place by an adhesive, or by stitching the element in place.

By employing a porous element having a laminate as described herein, numerous advantages are realized. For example, not only does the laminate material 44 act as a structural insert that prevents the side walls of the body from pulling apart during squeezing of the gripping members, but the material also presents a physical barrier that resists puncture by glass fragments of the fractured ampule. In addition, the laminate material provides a suitable welding material for securing the porous element in place on the body when an ultrasonic welding operation is used to manufacture the applicator.

In use, the applicator is designed to be grasped by the user so that the gripping members 24, 26 are held between the thumb or palm and fingers of one hand of the user. The members 24, 26 preferably include the ribs 28 and textured regions 32 to facilitate handling of the applicator 10 and to inhibit slippage from the user's hand. The ampule 14 is fractured by the user squeezing or pivoting the gripping members 24, 26 toward one another. The pivoting movement of the members 24, 26 is transferred by the tappets 36, 38, 40 to the pocket 18 to deform the pocket 18 inwardly and exert discrete localized fracturing forces against the ampule 14.

The gripping members 24, 26 provide a lever action that gains mechanical advantage as the members 24, 26 are pivoted towards one another about the flange. Accordingly, if the user has limited gripping strength, or if the wall of the ampule 14 is exceptionally thick, the members 24, 26 ensure fracturing of the ampule 14. In the absence of the structural insert defined by the laminate material 44 of the porous element 16, the side walls of the body would be unrestricted from pulling apart from one another when the gripping members are squeezed, and such movement would mitigate the mechanical advantage intended by the preferred construction. However, the provision of the laminate material secured to and between the side walls ensures that the maximum possible mechanical advantage is realized upon squeezing of the gripping members.

As shown in FIG. 6, once the members 24, 26 have been sufficiently pivoted, the resulting forces fracture the ampule 14 releasing the liquid contained therein. At the same time, the retaining tappet 40 forces the ampule 14 away from the open side of the pocket 18 during fracturing which directs shards of glass away from the porous element 16. Once the ampule 14 is fractured, liquid flows from the ampule 14 to the pocket 18 and ultimately into the porous element 16. The saturated element 16 is then brought into contact with a surface to apply the liquid thereto.

Although the invention has been described with reference to the preferred embodiment illustrated in the attached drawing figures, it is understood that substitutions may be made and equivalents employed herein without departing from the scope of the invention as recited in the claims.

What is claimed is:

1. A liquid applicator comprising:
    a body including a pair of side walls that are spaced from one another in a first direction to define a pocket;
    a closed ampule received in the pocket, the ampule being formed of a fracturable material and containing a liquid to be dispensed;
    a lever presenting a first end secured to one of the side walls, a second free end, and an intermediate tappet that bears against the body and fractures the ampule when the lever is pivoted; and
    a porous element covering the pocket so that liquid flows through the porous element when the ampule is fractured, the porous element being laminated with a material that does not stretch in the first direction, the laminate material being secured directly to the side walls of the body to prevent the side walls from pulling apart from one another when the lever is pivoted.

2. A liquid applicator as recited in claim 1, wherein the body is elongated, defining a longitudinal axis extending transverse to the first direction, the laminate material of the porous element being stretchable along the longitudinal axis.

3. A liquid applicator as recited in claim 2, wherein the laminate material is a fabric.

4. A liquid applicator as recited in claim 2, wherein the laminate material is a polyester fabric.

5. A liquid applicator as recited in claim 1, wherein the ampule is formed of glass and the laminate material of the porous element resists puncture by fragments of the glass from the fractured ampule.

6. A liquid applicator as recited in claim 1, wherein levers are secured to both side walls, each lever including a first end secured to one of the side walls, a second free end, and an intermediate tappet that bears against the body and fractures the ampule when the lever is pivoted.

7. A liquid applicator as recited in claim 1, wherein the laminate material and the material of the body are melted together to secure the porous element to the body.

* * * * *